United States Patent [19]

Beattie

[11] 4,430,245

[45] Feb. 7, 1984

[54] SOAP COMPOSITION

[75] Inventor: Ian A. M. Beattie, Birkenhead, England

[73] Assignee: Internationale Octrooi Maatschappij "Octropa" B.V., Rotterdam, Netherlands

[21] Appl. No.: 251,703

[22] Filed: Apr. 6, 1981

[51] Int. Cl.$^3$ .................. C11D 9/30; C11D 15/04; C11D 9/22
[52] U.S. Cl. .................................. 252/117; 252/118; 252/132; 252/DIG. 5; 252/DIG. 14
[58] Field of Search ......... 252/117, 118, 132, DIG. 5, 252/DIG. 14

[56] References Cited

U.S. PATENT DOCUMENTS

| | | | |
|---|---|---|---|
| 2,551,634 | 5/1951 | Price | 252/118 |
| 3,553,138 | 1/1971 | Mace | 252/118 X |
| 3,703,481 | 11/1972 | Barker et al. | 252/117 X |
| 4,129,515 | 12/1978 | Foster | 252/117 |
| 4,288,225 | 9/1981 | Roland et al. | 252/117 X |
| 4,310,433 | 1/1982 | Stiros | 252/108 X |
| 4,312,771 | 1/1982 | Matsuda | 252/108 X |

FOREIGN PATENT DOCUMENTS

| | | |
|---|---|---|
| 2400453 | 7/1974 | Fed. Rep. of Germany . |
| 1188627 | 9/1959 | France . |
| 130945 | 5/1978 | German Democratic Rep. . |
| 1403691 | 8/1975 | United Kingdom . |

OTHER PUBLICATIONS

*McCutcheon's Detergents & Emulsifiers*, North American, 1978, p. 202.
Schimmel Briefs, Nov., 1955, No. 248.
Sagerin's Cosmetic Science & Technology, 1972, p. 88.

*Primary Examiner*—Michael R. Lusignan
*Attorney, Agent, or Firm*—Cushman, Darby & Cushman

[57] ABSTRACT

An aqueous liquid or semi-liquid soap composition, for use for example as a shower or bath product, is in the form of a single liquid phase which is preferably transparent. The composition comprises soap chosen from monoethanolamine soaps, diethanolamine soaps or mixtures thereof, and a thickening agent chosen from $C_{12}$ to $C_{18}$ fatty acids, $C_{12}$ to $C_{18}$ fatty acid alkanolamides or mixtures thereof.

4 Claims, No Drawings

SOAP COMPOSITION

The invention relates to a liquid soap composition, and more particularly to compositions in which the soap component comprises soap other than sodium soap.

Aqueous liquid soap products containing sodium soap as the main soap ingredient tend to be unstable and readily form heterogenous gels even at low soap concentrations of up to 5% by weight. It is for this reason that the more soluble soaps, especially those based on potassium, ammonium, and tri-ethanolamines are generally employed in the manufacture of water-based liquid soaps.

When thickening aqueous liquid soaps, it is not possible to use sodium chloride such as is traditionally employed in the thickening of liquid non-soap detergents because the soaps tend to precipitate.

As an alternative, aqueous liquid soaps can be thickened by increasing the concentration of the more soluble soaps, or by addition of fatty acid ethanolamides or free fatty acids, but these methods of thickening are not without problems, since in the presence of certain perfumes as commonly employed in soap manufacture, phase separation can occur, particularly when the viscosity exceeds 2000 cps.

It has now been discovered that thickened aqueous liquid soaps having a viscosity greater than 2000 cps, and even as high as 10,000 cps can be obtained, without the aforementioned problem of phase separation, by selection of a specific soap for the composition.

Accordingly, the invention provides an aqueous liquid soap composition comprising a single liquid phase containing soap chosen from monoethanolamine soaps, diethanolamine soaps and mixtures thereof, and a thickening agent chosen from $C_{12}$ to $C_{18}$ fatty acids, $C_{12}$ to $C_{18}$ fatty acid alkanolamides and mixtures thereof.

The invention also provides a process for preparing an aqueous liquid soap composition comprising a single liquid phase, which process comprises mixing together soap chosen from monoethanolamine soaps, diethanolamine soaps and mixtures thereof, and a thickening agent chosen from $C_{12}$ to $C_{18}$ fatty acids, $C_{12}$ to $C_{18}$ fatty acid alkanolamides and mixtures thereof.

It should be explained that the liquid soap compositions of the invention include flowable liquids and gels comprising a single liquid phase which is preferably water-clear.

The soap component of the composition is a water-soluble or water-dispersible soap chosen from monoethanolamine and/or diethanolamine-soaps of fatty acids.

The fatty acid moiety of the monoethanolamine and/or diethanolamine soaps will normally be derived from a mixture of fatty acids having a carbon chain of from 10 to 18 carbon atoms. Preferably, these fatty acids comprise saturated fatty acids.

The preferred soap is a soap of coconut fatty acids, that is fatty acids derived from coconut class oils, for example, coconut, palm kernel and babacue oils. Minor amounts of up to 30%, preferably 10 to 20% by weight of soaps of tallow class fatty acids derived from tallow, may be admixed with the coconut fatty acid soaps to improve their lathering and solubility characteristics if desired. Whereas tallow fatty acids are predominantly $C_{16}$ to $C_{18}$ fatty acids, the coconut oil fatty acids are of shorter chain length and are predominantly $C_{10}$ to $C_{14}$ fatty acids.

The amount of soap employed in the composition is from 5 to 30%, preferably from 10 to 25% by weight of the composition.

Compositions containing less than 5% of the soap are unlikely to produce sufficient lather and be incapable of adequate cleansing in use, whereas compositions containing more than 30% by weight of soap are likely to suffer from the disadvantage that phase separation can occur on storage, with the result that the aqueous liquid soap develops a heterogenous granular appearance.

It is also possible optionally to employ a small quantity of sodium soap in the composition, provided that the single liquid phase character of the composition is maintained and provided that no substantial precipitation occurs.

When the sodium soap is employed, it will generally be present in the composition at a concentration of not greater than 2%.

The aqueous liquid soap composition also comprises $C_{12}$ to $C_{18}$ fatty acid or $C_{12}$ to $C_{18}$ fatty acid alkanolamide, or a mixture thereof as a thickening agent, instead of conventional thickeners such as sodium chloride or sodium sulphate as are used in liquid one-soap detergents. The fatty acid alkanolamide can also aid the solubilisation of perfume that is commonly employed in the formulation.

The preferred alkanolamide is coconut fatty acid diethanolamide, and the preferred fatty acid is coconut type fatty acid.

The amount of fatty acid or fatty acid alkanolamide, or a mixture thereof, that can optionally be employed is from 0.5 to 5%, preferably 1 to 4% and ideally about 2% by weight of the composition.

If less than 0.5% by weight of the fatty acid and/or fatty acid alkanolamide is employed, it is likely that the composition will be unsufficiently thickened. If on the other hand, more than 5% by weight of fatty acid and/or fatty acid alkanolamide is employed, the composition may be too thick for use as a liquid product. This is however not necessarily a disadvantage if a gel product is required. More than 5% by weight of the fatty acid alkanolamide can cause phase separation giving an otherwise transparent product an opaque or turbid appearance due to separated perfume.

The composition can also optionally include other ingredients conventionally used in soap such as lather boosters, hemectants such as glycerine, moisturisers, colourants and opacifiers.

A particularly preferred opacifier that can be employed when an opaque rather than a transparent soap composition is desired is ethylene glycol mono- or distearate, for example in the form of a 20% solution in sodium lauryl ether sulphate. An alternative opacifying agent is zinc stearate.

Products of the invention can be prepared by mixing together the above-defined ingredients in the amounts as specified herein. It is however convenient for form the monoethanolamine soap and/or the diethanolamine soap by mixing together mono- and/or diethanolamine with free fatty acids in the appropriate stochiometric proportions, or with a slight excess of the fatty acids. Excess of the fatty acids added for this purpose can also function as thickening agent in the manner herein described.

The product can take the form of a water-clear, i.e. transparent, liquid soap, in which case it will not contain an opacifier, or alternatively, it can take the form of an opaque liquid soap containing an opacifier such as that herein defined.

The compositions of the invention can be used for personal or fabric washing. Examples of personal washing products are liquid soaps for use in handwashing dispenser, or as liquid or gel shower products.

The invention is illustrated by the following examples which exemplify liquid soap products for personal and fabric washing.

EXAMPLE 1

This Example illustrates a shower gel product.

A shower gel product was prepared by mixing together the following ingredients:

|  | % w/w |
|---|---|
| Monoethanolamine soap of fatty acids in the range $C_{12}$ to $C_{18}$ | 14.2 |
| Fatty acids in the range $C_{12}$ to $C_{18}$ | 3.0 |
| Coconut fatty acid diethanolamide | 2.5 |
| Glycerol | 0.5 |
| Perfume | 1.5 |
| Distilled water | 78.3 |

The shower gel had a pH value of between 8.5 and 9.0 and a viscosity of from 2,000 to 6,000 cps.

EXAMPLE 2

This Example illustrates a shower gel product.

A shower gel product can be prepared by mixing together the following ingredients:

|  | % w/w |
|---|---|
| Diethanolamine soap of fatty acids in the range $C_{12}$ to $C_{18}$ | 16.7 |
| Fatty acids in the range $C_{12}$ to $C_{18}$ | 3.0 |
| Coconut diethanolamide | 3.0 |
| Glycerol | 0.8 |
| Perfume | 1.5 |
| Distilled water | 75.0 |

The shower gel will have a pH value of between 8 and 9.5 and a viscosity of from 2,000 to 7,000 cps.

EXAMPLE 3

This Example illustrates a liquid fabric washing product.

A liquid fabric washing product can be prepared by mixing together the following ingredients:

|  | % w/w |
|---|---|
| Monoethanolamine soap of fatty acids in the range $C_{12}$ to $C_{18}$ | 19.8 |
| Potassium soap of fatty acids in the range $C_{12}$ to $C_{18}$ | 4.2 |
| Coconut fatty acid diethanolamide | 3.5 |
| Ethanol | 5.0 |
| Perfume | 0.5 |
| Fluorescer and colouring matter | 0.9 |
| Water | 66.1 |

The liquid product can be employed for washing fabrics, particularly woollen garments by dilution with water in an amount of from 1 part liquid product to 100 to 500 parts water.

EXAMPLE 4

This Example illustrates a liquid soap product suitable for personal washing.

A liquid soap personal washing product was prepared from the following ingredients:

|  | % w/w |
|---|---|
| Lauric acid | 8.5 |
| Myristic acid | 3.0 |
| Stearine | 3.0 |
| Monoethanolamine | 3.7 |
| Chelating agent | 0.1 |
| Anti oxidant | 0.02 |
| Perfume | 1.2 |
| Coconut fatty acid diethanolamide | 2.5 |
| Colouring matter | 0.001 |
| Water | 77.979 |

The liquid soap personal washing product was prepared by mixing together the free fatty acids and the monoethanolamine to form the corresponding monoethanolamine soap of these fatty acids. The remaining ingredients were incorporated by careful mixing to provide the finished product which is suitable for personal washing.

What is claimed is:

1. A thickened single liquid phase aqueous soap composition having a viscosity of from 2000 to 10,000 cps, said composition comprising in addition to water:
   (i) from about 10 to about 25% by weight of a water-soluble or water-dispersible fatty acid soap selected from the group consisting of monoethanolamine fatty acid soaps, diethanolamine fatty acid soaps and mixtures thereof, the fatty acid moiety being derived from a mixture of fatty acids having a carbon chain of from 10 to 18 carbon atoms, the fatty acids being predominantly $C_{10}$ to $C_{14}$;
   (ii) a first thickening agent selected from the group consisting of $C_{12}$ to $C_{18}$ fatty acid alkanolamides and mixtures thereof;
   (iii) a second thickening agent selected from the group consisting of $C_{12}$ to $C_{18}$ fatty acids and mixtures thereof, the first and second thickening agents together forming from about 1% to about 4% by weight of the composition; and
   (iv) an effective amount of a perfume, the composition being characterized by its freedom from the problem of phase separation which may occur with other aqueous liquid soap compositions which have a viscosity exceeding 2000 cps and contain a perfume in combination with a soap other than as defined in (i).

2. The composition of claim 1, wherein the $C_{12}$ to $C_{18}$ fatty acids comprise saturated fatty acids.

3. The composition of claim 1, wherein the fatty acid alkanolamide is coconut fatty acid diethanolamide.

4. The composition of claim 1, in the form of a shower gel.

* * * * *